US005518724A

United States Patent [19]

Snyder et al.

[11] Patent Number: 5,518,724

[45] Date of Patent: May 21, 1996

[54] INFECTIOUS BURSAL DISEASE VIRUS

[75] Inventors: David B. Snyder, deceased, late of Bowie, by Nancy Snyder, legal representative; Vikram Vakharia, Bowie, both of Md.

[73] Assignee: University of Maryland, College Park, Md.

[21] Appl. No.: 944,943

[22] Filed: Sep. 15, 1992

Related U.S. Application Data

[63] Continuation-in-part of Ser. No. 727,370, Jul. 9, 1991, abandoned, which is a continuation of Ser. No. 423,757, Oct. 18, 1989, abandoned, which is a continuation-in-part of Ser. No. 227,311, Aug. 2, 1988, Pat. No. 5,064,646.

[51] Int. Cl.[6] .............................. A61K 39/12; C12N 7/00; C12N 7/02; C12N 7/04

[52] U.S. Cl. .................... 424/204.1; 424/816; 435/235.1; 435/236; 435/237; 435/238; 435/239

[58] Field of Search ................................ 435/235.1, 236, 435/237, 238, 239; 424/204.1, 826, 816

[56] References Cited

U.S. PATENT DOCUMENTS

| | | | |
|---|---|---|---|
| 4,530,831 | 7/1985 | Lutticken et al. | 424/202.1 |
| 4,824,668 | 4/1989 | Melchoir et al. | 424/202.1 |
| 5,064,646 | 11/1991 | Snyder et al. | 424/147.1 |

FOREIGN PATENT DOCUMENTS

| | | |
|---|---|---|
| WO90/01336 | 2/1990 | WIPO . |

OTHER PUBLICATIONS

Bowie et al, Science 247:1306–1310 Mar. 1990.

Kumar et al. PNAS 87:1337–41 Feb. 1990.

*Primary Examiner*—Mary E. Mosher
*Assistant Examiner*—Anthony Caputa
*Attorney, Agent, or Firm*—Oblon, Spivak, McClelland, Maier, & Neustadt

[57] ABSTRACT

A new virus not neutralized or bound by monoclonal antibodies which are group neutralizing to all IBDV vaccines of current art, and capable of inducing infectious bursal disease in poultry is identified, in essentially pure form. A test kit, and assay for the presence of the virus is disclosed, together with the vaccine incorporating the virus. A monoclonal antibody Mab 50, which neutralizes the virus, form the basis of an alternative vaccine.

3 Claims, 6 Drawing Sheets

```
           10          20          30          40          50
GAA TTC CTC CTT CTA CAA TGC TAT CAT TGA TGG TTA GTA GAG ATC GGA CAA ACG
--- --- --- --- --- --- --- --- --- --- --- --- --- --- --- --- --- ---
     60          70          80          90          100
ATC GCA GCG ATG ACA AAC CTG CAA GAT CAA ACC CAA CAG ATT GTT CCG TTC ATA
--- --- --- MET Thr Asn Leu Gln Asp Gln Thr Gln Gln Ile Val Pro Phe Ile
110         120         130         140         150         160
CGG AGC CTT CTG ATG CCA ACA ACC GGA CCG GCG TCC ATT CCG GAC GAC ACC CTG
Arg Ser Leu Leu MET Pro Thr Thr Gly Pro Ala Ser Ile Pro Asp Asp Thr Leu
        170         180         190         200         210
GAG AAG CAC ACT CTC AGG TCA GAG ACC TCG ACC TAC AAT TTG ACT GTG GGG GAC
Glu Lys His Thr Leu Arg Ser Glu Thr Ser Thr Tyr Asn Leu Thr Val Gly Asp
   220         230         240         250         260         270
ACA GGG TCA GGG CTA ATT GTC TTT TTC CCT GGA TTC CCT GGC TCA ATT GTG GGT
Thr Gly Ser Gly Leu Ile Val Phe Phe Pro Gly Phe Pro Gly Ser Ile Val Gly
           280         290         300         310         320
GCT CAC TAC ACA CTG CAG AGC AAT GGG AAC TAC AAG TTC GAT CAG ATG CTC CTG
Ala His Tyr Thr Leu Gln Ser Asn Gly Asn Tyr Lys Phe Asp Gln MET Leu Leu
     330         340         350         360         370
ACT GCC CAG AAC CTA CCG GCC AGC TAC AAC TAC TGC AGG CTA GTG AGT CGG AGT
Thr Ala Gln Asn Leu Pro Ala Ser Tyr Asn Tyr Cys Arg Leu Val Ser Arg Ser
380         390         400         410         420         430
CTC ACA GTA AGG TCA AGC ACA CTC CCT GGT GGC GTT TAT GCA CTA AAC GGC ACC
Leu Thr Val Arg Ser Ser Thr Leu Pro Gly Gly Val Tyr Ala Leu Asn Gly Thr
```

*FIG. 1*

440 450 460 470 480
ATA AAC GCC GTG ACC TTC CAA GGA AGC CTG AGT GAA CTG ACA GAT GTT AGC TAC
Ile Asn Ala Val Thr Phe Gln Gly Ser Leu Ser Glu Leu Thr Asp Val Ser Tyr 490 500 510 520 530 540
AAT GGG TTG ATG TCT GCA ACA GCC AAC ATC AAC GAC AAA ATC GGG AAC GTC CTA
Asn Gly Leu MET Ser Ala The Ala Asn Ile Asn Asp Lys Ile Gly Asn Val Leu 550 560 570 580 590
GTA GGG GAA GGG GTC ACC GTC CTC AGC TTA CCC ACA TCA TAT GAT CTT GGG TAT
Val Gly Glu Gly Val Thr Val Leu Ser Leu Pro Thr Ser Tyr Asp Leu Gly Tyr 600 610 620 630 640
GTG AGG CTT GGT GAC CCC ATA CCC GCT ATA GGG CTT GAC CCA AAA ATG GTA GCA
Val Arg Leu Gly Asp Pro Ile Pro Ala Ile Gly Leu Asp Pro Lys MET Val Ala 650 660 670 680 690 700
ACA TGT GAC AGC AGT GAC AGG CCC AGA GTC TAC ACC ATA ACT GCA GCC GAT GAT
Thr Cys Asp Ser Ser Asp Arg Pro Arg Val Tyr Thr Ile Thr Ala Ala Asp Asp 710 720 730 740 750
TAC CAA TTC TCA TCA CAG TAC CAA TCA GGT GGG GTA ACA ATC ACA CTG TTC TCA
Tyr Gln Phe Ser Ser Gln Tyr Gln Ser Gly Gly Val Thr Ile Thr Leu Phe Ser 760 770 780 790 800 810
GCC AAC ATT GAT GCC ATC ACA AGC CTC AGC GTT GGG GGA GAG CTC CTG TTT AAA
Ala Asn Ile Asp Ala Ile Thr Ser Leu Ser Val Gly Gly Glu Leu Val Phe Lys 820 830 840 850 860
ACA AGC GTC CAA AGC CTT GTA CTG GGC GCC ACC ATC TAC CTC ATA GGC TTT GAT
Thr Ser Val Gln Ser Leu Val Leu Gly Ala Thr Ile Tyr Leu Ile Gly Phe Asp 870 880 890 900 910
GGG ACT GCG GTA ATC ACT AGA GCT GTG GCC GCG AAC AAT GGG CTG ACG GCC GGC
Gly Thr Ala Val Ile Thr Arg Ala Val Ala Ala Asn Asn Gly Leu Thr Ala Gly 920 930 940 950 960 970
ACC GAC AAT CTT ATG CCA TTC AAT CTT GTG ATT CCA ACC AAC GAG ATA ACC CAG
Thr Asp Asn Leu MET Pro Phe Asn Leu Val Ile Pro Thr Asn Glu Ile Thr Gln 980 990 1000 1010 1020
CCA ATC ACA TCC ATC AAA CTG AAG ATT GTG ACC TCC AAA AGT GGT GGT CTG GAA
Pro Ile Thr Ser Ile Lys Leu Lys Ile Val Thr Ser Lys Ser Gly Gly Leu Glu

*FIG. 1A*

```
     1030        1040        1050        1060        1070        1080
      |           |           |           |           |           |
GGG GAT CAG ATG TCA TGG TCG GCA AGT GGG AGC CTA GCA GTG ACG ATC CAT GGT
Gly Asp Gln MET Ser Trp Ser Ala Ser Gly Ser Leu Ala Val Thr Ile His Gly
            1090        1100        1110        1120        1130
             |           |           |           |           |
GGC AAC TAT CCA GGG GCC CTC CGT CCC GTC ACA CTA GTA GCC TAC GAA AGA GTG
Gly Asn Tyr Pro Gly Ala Leu Arg Pro Val Thr Leu Val Ala Tyr Glu Arg Val
        1140        1150        1160        1170        1180
         |           |           |           |           |
GCA ACA GGA TCT GTC GTT ACG GTC GCT GGG GTG AGC AAC TTC GAG CTG ATC CCA
Ala Thr Gly Ser Val Val Thr Val Ala Gly Val Ser Asn Phe Glu Leu Ile Pro
 1190        1200        1210        1220        1230        1240
  |           |           |           |           |           |
AAT CCT GAA CTA GCA AAG AAC CTG GTT ACA GAA TAC GGC CGA TTT GAC CCA GGA
Asn Pro Glu Leu Ala Lys Asn Leu Val Thr Glu Tyr Gly Arg Phe Asp Pro Gly
            1250        1260        1270        1280        1290
             |           |           |           |           |
GCC ATG AAC TAC ACA AAA TTG ATA CTG AGT GAG AGG GAC CGC CTT GGC ATC AAG
Ala MET Asn Tyr Thr Lys Leu Ile Leu Ser Glu Arg Asp Arg Leu Gly Ile Lys
    1300        1310        1320        1330        1340        1350
     |           |           |           |           |           |
ACC GTC TGG CCA ACA AGG GAG TAC ACT GAC TTT CGT GAG TAC TTC ATG GAG GTG
Thr Val Trp Pro Thr Arg Glu Tyr Thr Asp Phe Arg Glu Tyr Phe MET Glu Val
            1360        1370        1380        1390        1400
             |           |           |           |           |
GCC GAC CTC AAC TCT CCC CTG AAG ATT GCA GGA GCA TTT GGC TTC AAA GAC ATA
Ala Asp Leu Asn Ser Pro Leu Lys Ile Ala Gly Ala Phe Gly Phe Lys Asp Ile
        1410        1420        1430        1440        1450
         |           |           |           |           |
ATC CGG GCC ATA AGG AGG ATA GCT GTG CCG GTG GTC TCT ACA TTG TTC CCA CCT
Ile Arg Ala Ile Arg Arg Ile Ala Val Pro Val Val Ser Thr Leu Phe Pro Pro
 1460        1470        1480        1490        1500        1510
  |           |           |           |           |           |
GCC GCT CCC CTA GCC CAT GCA ATT GGG GAA GGT GTA GAC TAC CTG CTG GGC GAT
Ala Ala Pro Leu Ala His Ala Ile Gly Glu Gly Val Asp Tyr Leu Leu Gly Asp
            1520        1530        1540        1550        1560
             |           |           |           |           |
GAG GCA CAG GCT GCT TCG GGA ACT GCT CGA GCC GCG TCA GGA AAA GCA AGG GCT
Glu Ala Gln Ala Ala Ser Gly Thr Ala Arg Ala Ala Ser Gly Lys Ala Arg Ala
    1570        1580        1590        1600        1610        1620
     |           |           |           |           |           |
GCC TCA GGC CGC ATA AGG CAG CTG ACT CTC GCC GCC GAC AAG GGG TAC GAG GTA
Ala Ser Gly Arg Ile Arg Gln Leu Thr Leu Ala Ala Asp Lys Gly Tyr Glu Val
```

*FIG. 1B*

```
            1630            1640            1650            1660            1670
             |               |               |               |               |
GTC GCG AAT CTA TTC CAG GTG CCC CAG AAT CCC GTA GTC GAC GGG ATT CTT GCA
Val Ala Asn Leu Phe Gln Val Pro Gln Asn Pro Val Val Asp Gly Ile Leu Ala
        1680            1690            1700            1710            1720
         |               |               |               |               |
TCA CCC GGG ATA CTC CGC GGT GCA CAC AAC CTC GAC TGC GTG TTA AGA GAG GGC
Ser Pro Gly Ile Leu Arg Gly Ala His Asn Leu Asp Cys Val Leu Arg Glu Gly
   1730            1740            1750            1760            1770            1780
    |               |               |               |               |               |
GCC ACG CTA TTC CCT GTG GTC ATC ACG ACA GTG GAA GAC GCC ATG ACA CCC AAA
Ala Thr Leu Phe Pro Val Val Ile Thr Thr Val Glu Asp Ala MET Thr Pro Lys
            1790            1800            1810            1820            1830
             |               |               |               |               |
GCA CTG AAC AGC AAA ATG TTT GCT GTC ATT GAA GGC GCG CGA GAA GAC CTC CAA
Ala Leu Asn Ser Lys MET Phe Ala Val Ile Glu Gly Ala Arg Glu Asp Leu Gln
        1840            1850            1860            1870            1880            1890
         |               |               |               |               |               |
CCT CCA TCT CAA AGA GGA TCC TTT ATA CGA ACT CTC TCC GGA CAC AGA GTC TAT
Pro Pro Ser Gln Arg Gly Ser Phe Ile Arg Thr Leu Ser Gly His Arg Val Tyr
            1900            1910            1920            1930            1940
             |               |               |               |               |
GGA TAT GCT CCA GAT GGG GTA CTT CCA CTG GAG ACT GGG AGA GAC TAC ACC GTT
Gly Tyr Ala Pro Asp Gly Val Leu Pro Leu Glu Thr Gly Arg Asp Tyr Thr Val
        1950            1960            1970            1980            1990
         |               |               |               |               |
GTC CCA ATA GAT GAT GTC TGG GAC GAC AGC ATT ATG CTG TCC AAA GAC CCC ATA
Val Pro Ile Asp Asp Val Trp Asp Asp Ser Ile MET Leu Ser Lys Asp Pro Ile
2000            2010            2020            2030            2040            2050
 |               |               |               |               |               |
CCC CCT ATT GTG GGA AAC AGT GGA AAC CTA GCC ATA GCT TAC ATG GAT GTG TTT
Pro Pro Ile Val Gly Asn Ser Gly Asn Leu Ala Ile Ala Tyr MET Asp Val Phe
        2060            2070            2080            2090            2100
         |               |               |               |               |
CGA CCC AAA GTC CCC ATC CAT GTG GCC ATG ACG GGA GCC CTC AAC GCT TAT GGC
Arg Pro Lys Val Pro Ile His Val Ala MET Thr Gly Ala Leu Asn Ala Tyr Gly
    2110            2120            2130            2140            2150            2160
     |               |               |               |               |               |
GAG ATT GAG AAA ATA AGC TTT AGA AGC ACC AAG CTC GCC ACT GCA CAC CGG CTT
Glu Ile Glu Lys Ile Ser Phe Arg Ser Thr Lys Leu Ala Thr Ala His Arg Leu
            2170            2180            2190            2200            2210
             |               |               |               |               |
GGC CTC AAG TTG GCT GGT CCC GGA GCA TTC GAC GTA AAC ACC GGG CCC AAC TGG
Gly Leu Lys Leu Ala Gly Pro Gly Ala Phe Asp Val Asn Thr Gly Pro Asn Trp
```

*FIG. 1C*

```
       2220        2230        2240        2250        2260
        |           |           |           |           |
GCA ACG TTC ATC AAA CGT TTC CCT CAC AAT CCA CGC GAC TGG GAC AGG CTC CCC
Ala Thr Phe Ile Lys Arg Phe Pro His Asn Pro Arg Asp Trp Asp Arg Leu Pro
   2270        2280        2290        2300        2310        2320
    |           |           |           |           |           |
TAC CTC AAC CTT CCA TAC CTT CCA CCC AAT GCA GGA CGC CAG TAC CAC CTT GCC
Tyr Leu Asn Leu Pro Tyr Leu Pro Pro Asn Ala Gly Arg Gln Tyr His Leu Ala
         2330        2340        2350        2360        2370
          |           |           |           |           |
ATG GCT GCA TCA GAG TTT AAA GAG ACC CCT GAA CTC GAG AGC GCC GTC AGA GCC
MET Ala Ala Ser Glu Phe Lys Glu Thr Pro Glu Leu Glu Ser Ala Val Arg Ala
    2380        2390        2400        2410        2420        2430
     |           |           |           |           |           |
ATG GAA GCA GCA GCC AAT GTG GAC CCA CTG TTC CAA TCT GCA CTC AGT GTG TTC
MET Glu Ala Ala Ala Asn Val Asp Pro Leu Phe Gln Ser Ala Leu Ser Val Phe
            2440        2450        2460        2470        2480
             |           |           |           |           |
ATG TGG CTG GAA GAG AAT GGG ATT GTG GCT GAC ATG GCC AAT TTC GCA CTC AGC
MET Trp Leu Glu Glu Asn Gly Ile Val Ala Asp MET Ala Asn Phe Ala Leu Ser
        2490        2500        2510        2520        2530
         |           |           |           |           |
GAC CCG AAC GCC CAT CGG ATG CGC AAT TTT CTT GCA AAC GCA CCA CAA GCA GGC
Asp Pro Asn Ala His Arg MET Arg Asn Phe Leu Ala Asn ALa Pro Gln Ala Gly
2540        2550        2560        2570        2580        2590
 |           |           |           |           |           |
AGC AAG TCG CAA AGG GCC AAG TAC GGG ACA GCA GGC TAC GGA GTG GAG GCC CGG
Ser Lys Ser Gln Arg Ala Lys Tyr Gly Thr Ala Gly Tyr Gly Val Glu Ala Arg
        2600        2610        2620        2630        2640
         |           |           |           |           |
GGC CCC ACA CCA GAG GAA GCA CAG AGG GAA AAA GAC ACA CGG ATC TCA AAG AAG
Gly Pro Thr Pro Glu Glu Ala Gln Arg Glu Lys Asp Thr Arg Ile Ser Lys Lys
    2650        2660        2670        2680        2690        2700
     |           |           |           |           |           |
ATG GAG ACC ATG GGC ATC TAC TTT GCA ACA CCA GAA TGG GTA GCA CTC AAT GGG
MET Glu Thr MET Gly Ile Tyr Phe Ala Thr Pro Glu Trp Val Ala Leu Asn Gly
            2710        2720        2730        2740        2750
             |           |           |           |           |
CAC CGA GGG CCA AGC CCC GGC CAG CTA AAG TAC TGG CAG AAC ACA CGA GAA ATA
His Arg Gly Pro Ser Pro Gly Gln Leu Lys Tyr Trp Gln Asn Thr Arg Glu Ile
        2760        2770        2780        2790        2800
         |           |           |           |           |
CCG GAC CCA AAC GAG GAC TAT CTA GAC TAC GTG CAT GCA GAG AAG AGC CGG TTG
Pro Asp Pro Asn Glu Asp Tyr Leu Asp Tyr Val His Ala Glu Lys Ser Arg Leu
```

*FIG. 1D*

```
2810       2820        2830       2840       2850        2860
|          |           |          |          |           |
GCA TCA GAA GAA CAA ATC CTA AAG GCA GCT ACG TCG ATC TAC GGG GCT CCA GGA
Ala Ser Glu Glu Gln Ile Leu Lys Ala Ala Thr Ser Ile Tyr Gly Ala Pro Gly
      2870       2880        2890       2900       2910
      |          |           |          |          |
CAG GCA GAG CCA CCC CAA GCT TTC ATA GAC GAA GTT GCC AAA GTC TAT GAA ATC
Gln Ala Glu Pro Pro Gln Ala Phe Ile Asp Glu Val Ala Lys Val Tyr Glu Ile
 2920       2930       2940        2950       2960       2970
 |          |          |           |          |          |
AAC CAT GGA CGT GGC CCT AAC CAA GAA CAG ATG AAA GAT CTG CTC TTG ACT GCA
Asn His Gly Arg Gly Pro Asn Gln Glu Gln MET Lys Asp Leu Leu Leu Thr Ala
      2980       2990       3000        3010       3020
      |          |          |           |          |
ATG GAG ATG AAG CAT CGC AAC CCC AGG CGG GCT CCA CCA AAG CCC AAG CCA AAA
MET Glu MET Lys His Arg Asn Pro Arg Arg Ala Pro Pro Lys Pro Lys Pro Lys
  3030       3040       3050       3060        3070
  |          |          |          |           |
CCC AAT GCT CCA ACA CAG AGA CCC CCT GGT CGG CTG GGC CGC TGG ATC AGG ACC
Pro Asn Ala Pro Thr Gln Arg Pro Pro Gly Arg Leu Gly Arg Trp Ile Arg Thr
3080       3090        3100       3110       3120        3130
|          |           |          |          |           |
GTC TCT GAT GAG GAC CTT GAG TGA GGC CCC TGG GGG TCT CCC GAC ACC ACC CGC
Val Ser Asp Glu Asp Leu Glu --- --- --- --- --- --- --- --- --- --- ---
      3140       3150        3160       3170       3180
      |          |           |          |          |
GCA GGC GTG GAC ACC AAT TCG GCC TTA CAA CAT CCC AAA TTG GAT CCG
--- --- --- --- --- --- --- --- --- --- --- --- --- --- --- ---
```

*FIG. 1E*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3180 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 64..3099

-continued ( x i ) SEQUENCE DESCRIPTION: SEQ ID NO:1:

```
GAATTCCTCC TTCTACAATG CTATCATTGA TGGTTAGTAG AGATCGGACA AACGATCGCA   60

GCG ATG ACA AAC CTG CAA GAT CAA ACC CAA CAG ATT GTT CCG TTC ATA    108
    Met Thr Asn Leu Gln Asp Gln Thr Gln Gln Ile Val Pro Phe Ile
      1               5                  10                  15

CGG AGC CTT CTG ATG CCA ACA ACC GGA CCG GCG TCC ATT CCG GAC GAC    156
Arg Ser Leu Leu Met Pro Thr Thr Gly Pro Ala Ser Ile Pro Asp Asp
                 20                  25                  30

ACC CTG GAG AAG CAC ACT CTC AGG TCA GAG ACC TCG ACC TAC AAT TTG    204
Thr Leu Glu Lys His Thr Leu Arg Ser Glu Thr Ser Thr Tyr Asn Leu
             35                  40                  45

ACT GTG GGG GAC ACA GGG TCA GGG CTA ATT GTC TTT TTC CCT GGA TTC    252
Thr Val Gly Asp Thr Gly Ser Gly Leu Ile Val Phe Phe Pro Gly Phe
         50                  55                  60

CCT GGC TCA ATT GTG GGT GCT CAC TAC ACA CTG CAG AGC AAT GGG AAC    300
Pro Gly Ser Ile Val Gly Ala His Tyr Thr Leu Gln Ser Asn Gly Asn
     65                  70                  75

TAC AAG TTC GAT CAG ATG CTC CTG ACT GCC CAG AAC CTA CCG GCC AGC    348
Tyr Lys Phe Asp Gln Met Leu Leu Thr Ala Gln Asn Leu Pro Ala Ser
 80                  85                  90                  95

TAC AAC TAC TGC AGG CTA GTG AGT CGG AGT CTC ACA GTA AGG TCA AGC    396
Tyr Asn Tyr Cys Arg Leu Val Ser Arg Ser Leu Thr Val Arg Ser Ser
                100                 105                 110

ACA CTC CCT GGT GGC GTT TAT GCA CTA AAC GGC ACC ATA AAC GCC GTG    444
Thr Leu Pro Gly Gly Val Tyr Ala Leu Asn Gly Thr Ile Asn Ala Val
            115                 120                 125

ACC TTC CAA GGA AGC CTG AGT GAA CTG ACA GAT GTT AGC TAC AAT GGG    492
Thr Phe Gln Gly Ser Leu Ser Glu Leu Thr Asp Val Ser Tyr Asn Gly
        130                 135                 140

TTG ATG TCT GCA ACA GCC AAC ATC AAC GAC AAA ATC GGG AAC GTC CTA    540
Leu Met Ser Ala Thr Ala Asn Ile Asn Asp Lys Ile Gly Asn Val Leu
    145                 150                 155

GTA GGG GAA GGG GTC ACC GTC CTC AGC TTA CCC ACA TCA TAT GAT CTT    588
Val Gly Glu Gly Val Thr Val Leu Ser Leu Pro Thr Ser Tyr Asp Leu
160                 165                 170                 175

GGG TAT GTG AGG CTT GGT GAC CCC ATA CCC GCT ATA GGG CTT GAC CCA    636
Gly Tyr Val Arg Leu Gly Asp Pro Ile Pro Ala Ile Gly Leu Asp Pro
                180                 185                 190

AAA ATG GTA GCA ACA TGT GAC AGC AGT GAC AGG CCC AGA GTC TAC ACC    684
Lys Met Val Ala Thr Cys Asp Ser Ser Asp Arg Pro Arg Val Tyr Thr
            195                 200                 205

ATA ACT GCA GCC GAT GAT TAC CAA TTC TCA TCA CAG TAC CAA TCA GGT    732
Ile Thr Ala Ala Asp Asp Tyr Gln Phe Ser Ser Gln Tyr Gln Ser Gly
        210                 215                 220

GGG GTA ACA ATC ACA CTG TTC TCA GCC AAC ATT GAT GCC ATC ACA AGC    780
Gly Val Thr Ile Thr Leu Phe Ser Ala Asn Ile Asp Ala Ile Thr Ser
    225                 230                 235

CTC AGC GTT GGG GGA GAG CTC GTG TTT AAA ACA AGC GTC CAA AGC CTT    828
Leu Ser Val Gly Gly Glu Leu Val Phe Lys Thr Ser Val Gln Ser Leu
240                 245                 250                 255

GTA CTG GGC GCC ACC ATC TAC CTC ATA GGC TTT GAT GGG ACT GCG GTA    876
Val Leu Gly Ala Thr Ile Tyr Leu Ile Gly Phe Asp Gly Thr Ala Val
                260                 265                 270

ATC ACT AGA GCT GTG GCC GCG AAC AAT GGG CTG ACG GCC GGC ACC GAC    924
Ile Thr Arg Ala Val Ala Ala Asn Asn Gly Leu Thr Ala Gly Thr Asp
            275                 280                 285

AAT CTT ATG CCA TTC AAT CTT GTG ATT CCA ACC AAC GAG ATA ACC CAG    972
Asn Leu Met Pro Phe Asn Leu Val Ile Pro Thr Asn Glu Ile Thr Gln
        290                 295                 300
```

-continued

| | | | | | | | | | | | | | | | | |
|---|---|---|---|---|---|---|---|---|---|---|---|---|---|---|---|---|
| CCA | ATC | ACA | TCC | ATC | AAA | CTG | AAG | ATT | GTG | ACC | TCC | AAA | AGT | GGT | GGT | 1020 |
| Pro | Ile | Thr | Ser | Ile | Lys | Leu | Lys | Ile | Val | Thr | Ser | Lys | Ser | Gly | Gly | |
| | 305 | | | | | 310 | | | | | 315 | | | | | |
| CTG | GAA | GGG | GAT | CAG | ATG | TCA | TGG | TCG | GCA | AGT | GGG | AGC | CTA | GCA | GTG | 1068 |
| Leu | Glu | Gly | Asp | Gln | Met | Ser | Trp | Ser | Ala | Ser | Gly | Ser | Leu | Ala | Val | |
| 320 | | | | | 325 | | | | | 330 | | | | | 335 | |
| ACG | ATC | CAT | GGT | GGC | AAC | TAT | CCA | GGG | GCC | CTC | CGT | CCC | GTC | ACA | CTA | 1116 |
| Thr | Ile | His | Gly | Gly | Asn | Tyr | Pro | Gly | Ala | Leu | Arg | Pro | Val | Thr | Leu | |
| | | | | 340 | | | | | 345 | | | | | 350 | | |
| GTA | GCC | TAC | GAA | AGA | GTG | GCA | ACA | GGA | TCT | GTC | GTT | ACG | GTC | GCT | GGG | 1164 |
| Val | Ala | Tyr | Glu | Arg | Val | Ala | Thr | Gly | Ser | Val | Val | Thr | Val | Ala | Gly | |
| | | 355 | | | | | | 360 | | | | | 365 | | | |
| GTG | AGC | AAC | TTC | GAG | CTG | ATC | CCA | AAT | CCT | GAA | CTA | GCA | AAG | AAC | CTG | 1212 |
| Val | Ser | Asn | Phe | Glu | Leu | Ile | Pro | Asn | Pro | Glu | Leu | Ala | Lys | Asn | Leu | |
| | | 370 | | | | 375 | | | | | | 380 | | | | |
| GTT | ACA | GAA | TAC | GGC | CGA | TTT | GAC | CCA | GGA | GCC | ATG | AAC | TAC | ACA | AAA | 1260 |
| Val | Thr | Glu | Tyr | Gly | Arg | Phe | Asp | Pro | Gly | Ala | Met | Asn | Tyr | Thr | Lys | |
| | 385 | | | | | 390 | | | | | 395 | | | | | |
| TTG | ATA | CTG | AGT | GAG | AGG | GAC | CGC | CTT | GGC | ATC | AAG | ACC | GTC | TGG | CCA | 1308 |
| Leu | Ile | Leu | Ser | Glu | Arg | Asp | Arg | Leu | Gly | Ile | Lys | Thr | Val | Trp | Pro | |
| 400 | | | | | 405 | | | | | 410 | | | | | 415 | |
| ACA | AGG | GAG | TAC | ACT | GAC | TTT | CGT | GAG | TAC | TTC | ATG | GAG | GTG | GCC | GAC | 1356 |
| Thr | Arg | Glu | Tyr | Thr | Asp | Phe | Arg | Glu | Tyr | Phe | Met | Glu | Val | Ala | Asp | |
| | | | | 420 | | | | | 425 | | | | | 430 | | |
| CTC | AAC | TCT | CCC | CTG | AAG | ATT | GCA | GGA | GCA | TTT | GGC | TTC | AAA | GAC | ATA | 1404 |
| Leu | Asn | Ser | Pro | Leu | Lys | Ile | Ala | Gly | Ala | Phe | Gly | Phe | Lys | Asp | Ile | |
| | | | 435 | | | | | 440 | | | | | 445 | | | |
| ATC | CGG | GCC | ATA | AGG | AGG | ATA | GCT | GTG | CCG | GTG | GTC | TCT | ACA | TTG | TTC | 1452 |
| Ile | Arg | Ala | Ile | Arg | Arg | Ile | Ala | Val | Pro | Val | Val | Ser | Thr | Leu | Phe | |
| | | 450 | | | | | 455 | | | | | 460 | | | | |
| CCA | CCT | GCC | GCT | CCC | CTA | GCC | CAT | GCA | ATT | GGG | GAA | GGT | GTA | GAC | TAC | 1500 |
| Pro | Pro | Ala | Ala | Pro | Leu | Ala | His | Ala | Ile | Gly | Glu | Gly | Val | Asp | Tyr | |
| | 465 | | | | | 470 | | | | | 475 | | | | | |
| CTG | CTG | GGC | GAT | GAG | GCA | CAG | GCT | GCT | TCG | GGA | ACT | GCT | CGA | GCC | GCG | 1548 |
| Leu | Leu | Gly | Asp | Glu | Ala | Gln | Ala | Ala | Ser | Gly | Thr | Ala | Arg | Ala | Ala | |
| 480 | | | | | 485 | | | | | 490 | | | | | 495 | |
| TCA | GGA | AAA | GCA | AGG | GCT | GCC | TCA | GGC | CGC | ATA | AGG | CAG | CTG | ACT | CTC | 1596 |
| Ser | Gly | Lys | Ala | Arg | Ala | Ala | Ser | Gly | Arg | Ile | Arg | Gln | Leu | Thr | Leu | |
| | | | | 500 | | | | | 505 | | | | | 510 | | |
| GCC | GCC | GAC | AAG | GGG | TAC | GAG | GTA | GTC | GCG | AAT | CTA | TTC | CAG | GTG | CCC | 1644 |
| Ala | Ala | Asp | Lys | Gly | Tyr | Glu | Val | Val | Ala | Asn | Leu | Phe | Gln | Val | Pro | |
| | | | 515 | | | | | 520 | | | | | 525 | | | |
| CAG | AAT | CCC | GTA | GTC | GAC | GGG | ATT | CTT | GCA | TCA | CCC | GGG | ATA | CTC | CGC | 1692 |
| Gln | Asn | Pro | Val | Val | Asp | Gly | Ile | Leu | Ala | Ser | Pro | Gly | Ile | Leu | Arg | |
| | | 530 | | | | | 535 | | | | | 540 | | | | |
| GGT | GCA | CAC | AAC | CTC | GAC | TGC | GTG | TTA | AGA | GAG | GGC | GCC | ACG | CTA | TTC | 1740 |
| Gly | Ala | His | Asn | Leu | Asp | Cys | Val | Leu | Arg | Glu | Gly | Ala | Thr | Leu | Phe | |
| | 545 | | | | | 550 | | | | | 555 | | | | | |
| CCT | GTG | GTC | ATC | ACG | ACA | GTG | GAA | GAC | GCC | ATG | ACA | CCC | AAA | GCA | CTG | 1788 |
| Pro | Val | Val | Ile | Thr | Thr | Val | Glu | Asp | Ala | Met | Thr | Pro | Lys | Ala | Leu | |
| 560 | | | | | 565 | | | | | 570 | | | | | 575 | |
| AAC | AGC | AAA | ATG | TTT | GCT | GTC | ATT | GAA | GGC | GCG | CGA | GAA | GAC | CTC | CAA | 1836 |
| Asn | Ser | Lys | Met | Phe | Ala | Val | Ile | Glu | Gly | Ala | Arg | Glu | Asp | Leu | Gln | |
| | | | | 580 | | | | | 585 | | | | | 590 | | |
| CCT | CCA | TCT | CAA | AGA | GGA | TCC | TTT | ATA | CGA | ACT | CTC | TCC | GGA | CAC | AGA | 1884 |
| Pro | Pro | Ser | Gln | Arg | Gly | Ser | Phe | Ile | Arg | Thr | Leu | Ser | Gly | His | Arg | |
| | | | 595 | | | | | 600 | | | | | 605 | | | |
| GTC | TAT | GGA | TAT | GCT | CCA | GAT | GGG | GTA | CTT | CCA | CTG | GAG | ACT | GGG | AGA | 1932 |
| Val | Tyr | Gly | Tyr | Ala | Pro | Asp | Gly | Val | Leu | Pro | Leu | Glu | Thr | Gly | Arg | |
| | | 610 | | | | | 615 | | | | | 620 | | | | |

-continued

| | | | | | | | | | | | | | | | | |
|---|---|---|---|---|---|---|---|---|---|---|---|---|---|---|---|---|
| GAC | TAC | ACC | GTT | GTC | CCA | ATA | GAT | GAT | GTC | TGG | GAC | GAC | AGC | ATT | ATG | 1980 |
| Asp | Tyr | Thr | Val | Val | Pro | Ile | Asp | Asp | Val | Trp | Asp | Asp | Ser | Ile | Met | |
| | 625 | | | | | 630 | | | | | 635 | | | | | |
| CTG | TCC | AAA | GAC | CCC | ATA | CCC | CCT | ATT | GTG | GGA | AAC | AGT | GGA | AAC | CTA | 2028 |
| Leu | Ser | Lys | Asp | Pro | Ile | Pro | Pro | Ile | Val | Gly | Asn | Ser | Gly | Asn | Leu | |
| 640 | | | | | 645 | | | | | 650 | | | | | 655 | |
| GCC | ATA | GCT | TAC | ATG | GAT | GTG | TTT | CGA | CCC | AAA | GTC | CCC | ATC | CAT | GTG | 2076 |
| Ala | Ile | Ala | Tyr | Met | Asp | Val | Phe | Arg | Pro | Lys | Val | Pro | Ile | His | Val | |
| | | | | 660 | | | | | 665 | | | | | 670 | | |
| GCC | ATG | ACG | GGA | GCC | CTC | AAC | GCT | TAT | GGC | GAG | ATT | GAG | AAA | ATA | AGC | 2124 |
| Ala | Met | Thr | Gly | Ala | Leu | Asn | Ala | Tyr | Gly | Glu | Ile | Glu | Lys | Ile | Ser | |
| | | | 675 | | | | | 680 | | | | | 685 | | | |
| TTT | AGA | AGC | ACC | AAG | CTC | GCC | ACT | GCA | CAC | CGG | CTT | GGC | CTC | AAG | TTG | 2172 |
| Phe | Arg | Ser | Thr | Lys | Leu | Ala | Thr | Ala | His | Arg | Leu | Gly | Leu | Lys | Leu | |
| | | 690 | | | | | 695 | | | | | 700 | | | | |
| GCT | GGT | CCC | GGA | GCA | TTC | GAC | GTA | AAC | ACC | GGG | CCC | AAC | TGG | GCA | ACG | 2220 |
| Ala | Gly | Pro | Gly | Ala | Phe | Asp | Val | Asn | Thr | Gly | Pro | Asn | Trp | Ala | Thr | |
| | 705 | | | | | 710 | | | | | 715 | | | | | |
| TTC | ATC | AAA | CGT | TTC | CCT | CAC | AAT | CCA | CGC | GAC | TGG | GAC | AGG | CTC | CCC | 2268 |
| Phe | Ile | Lys | Arg | Phe | Pro | His | Asn | Pro | Arg | Asp | Trp | Asp | Arg | Leu | Pro | |
| 720 | | | | | 725 | | | | | 730 | | | | | 735 | |
| TAC | CTC | AAC | CTT | CCA | TAC | CTT | CCA | CCC | AAT | GCA | GGA | CGC | CAG | TAC | CAC | 2316 |
| Tyr | Leu | Asn | Leu | Pro | Tyr | Leu | Pro | Pro | Asn | Ala | Gly | Arg | Gln | Tyr | His | |
| | | | | 740 | | | | | 745 | | | | | 750 | | |
| CTT | GCC | ATG | GCT | GCA | TCA | GAG | TTT | AAA | GAG | ACC | CCT | GAA | CTC | GAG | AGC | 2364 |
| Leu | Ala | Met | Ala | Ala | Ser | Glu | Phe | Lys | Glu | Thr | Pro | Glu | Leu | Glu | Ser | |
| | | | 755 | | | | | 760 | | | | | 765 | | | |
| GCC | GTC | AGA | GCC | ATG | GAA | GCA | GCA | GCC | AAT | GTG | GAC | CCA | CTG | TTC | CAA | 2412 |
| Ala | Val | Arg | Ala | Met | Glu | Ala | Ala | Ala | Asn | Val | Asp | Pro | Leu | Phe | Gln | |
| | | 770 | | | | | 775 | | | | | 780 | | | | |
| TCT | GCA | CTC | AGT | GTG | TTC | ATG | TGG | CTG | GAA | GAG | AAT | GGG | ATT | GTG | GCT | 2460 |
| Ser | Ala | Leu | Ser | Val | Phe | Met | Trp | Leu | Glu | Glu | Asn | Gly | Ile | Val | Ala | |
| | 785 | | | | | 790 | | | | | 795 | | | | | |
| GAC | ATG | GCC | AAT | TTC | GCA | CTC | AGC | GAC | CCG | AAC | GCC | CAT | CGG | ATG | CGA | 2508 |
| Asp | Met | Ala | Asn | Phe | Ala | Leu | Ser | Asp | Pro | Asn | Ala | His | Arg | Met | Arg | |
| 800 | | | | | 805 | | | | | 810 | | | | | 815 | |
| AAT | TTT | CTT | GCA | AAC | GCA | CCA | CAA | GCA | GGC | AGC | AAG | TCG | CAA | AGG | GCC | 2556 |
| Asn | Phe | Leu | Ala | Asn | Ala | Pro | Gln | Ala | Gly | Ser | Lys | Ser | Gln | Arg | Ala | |
| | | | | 820 | | | | | 825 | | | | | 830 | | |
| AAG | TAC | GGG | ACA | GCA | GGC | TAC | GGA | GTG | GAG | GCC | CGG | GGC | CCC | ACA | CCA | 2604 |
| Lys | Tyr | Gly | Thr | Ala | Gly | Tyr | Gly | Val | Glu | Ala | Arg | Gly | Pro | Thr | Pro | |
| | | | 835 | | | | | 840 | | | | | 845 | | | |
| GAG | GAA | GCA | CAG | AGG | GAA | AAA | GAC | ACA | CGG | ATC | TCA | AAG | AAG | ATG | GAG | 2652 |
| Glu | Glu | Ala | Gln | Arg | Glu | Lys | Asp | Thr | Arg | Ile | Ser | Lys | Lys | Met | Glu | |
| | | 850 | | | | | 855 | | | | | 860 | | | | |
| ACC | ATG | GGC | ATC | TAC | TTT | GCA | ACA | CCA | GAA | TGG | GTA | GCA | CTC | AAT | GGG | 2700 |
| Thr | Met | Gly | Ile | Tyr | Phe | Ala | Thr | Pro | Glu | Trp | Val | Ala | Leu | Asn | Gly | |
| | 865 | | | | | 870 | | | | | 875 | | | | | |
| CAC | CGA | GGG | CCA | AGC | CCC | GGC | CAG | CTA | AAG | TAC | TGG | CAG | AAC | ACA | CGA | 2748 |
| His | Arg | Gly | Pro | Ser | Pro | Gly | Gln | Leu | Lys | Tyr | Trp | Gln | Asn | Thr | Arg | |
| 880 | | | | | 885 | | | | | 890 | | | | | 895 | |
| GAA | ATA | CCG | GAC | CCA | AAC | GAG | GAC | TAT | CTA | GAC | TAC | GTG | CAT | GCA | GAG | 2796 |
| Glu | Ile | Pro | Asp | Pro | Asn | Glu | Asp | Tyr | Leu | Asp | Tyr | Val | His | Ala | Glu | |
| | | | | 900 | | | | | 905 | | | | | 910 | | |
| AAG | AGC | CGG | TTG | GCA | TCA | GAA | GAA | CAA | ATC | CTA | AAG | GCA | GCT | ACG | TCG | 2844 |
| Lys | Ser | Arg | Leu | Ala | Ser | Glu | Glu | Gln | Ile | Leu | Lys | Ala | Ala | Thr | Ser | |
| | | | 915 | | | | | 920 | | | | | 925 | | | |
| ATC | TAC | GGG | GCT | CCA | GGA | CAG | GCA | GAG | CCA | CCC | CAA | GCT | TTC | ATA | GAC | 2892 |
| Ile | Tyr | Gly | Ala | Pro | Gly | Gln | Ala | Glu | Pro | Pro | Gln | Ala | Phe | Ile | Asp | |
| | | 930 | | | | | 935 | | | | | 940 | | | | |

-continued

GAA GTT GCC AAA GTC TAT GAA ATC AAC CAT GGA CGT GGC CCT AAC CAA 2940
Glu Val Ala Lys Val Tyr Glu Ile Asn His Gly Arg Gly Pro Asn Gln
945 950 955

GAA CAG ATG AAA GAT CTG CTC TTG ACT GCA ATG GAG ATG AAG CAT CGC 2988
Glu Gln Met Lys Asp Leu Leu Leu Thr Ala Met Glu Met Lys His Arg
960 965 970 975

AAC CCC AGG CGG GCT CCA CCA AAG CCC AAG CCA AAA CCC AAT GCT CCA 3036
Asn Pro Arg Arg Ala Pro Pro Lys Pro Lys Pro Lys Pro Asn Ala Pro
980 985 990

ACA CAG AGA CCC CCT GGT CGG CTG GGC CGC TGG ATC AGG ACC GTC TCT 3084
Thr Gln Arg Pro Pro Gly Arg Leu Gly Arg Trp Ile Arg Thr Val Ser
995 1000 1005

GAT GAG GAC CTT GAG TGAGGCCCCT GGGGGTCTCC CGACACCACC CGCGCAGGCG 3139
Asp Glu Asp Leu Glu
1010

TGGACACCAA TTCGGCCTTA CAACATCCCA AATTGGATCC G 3180

( 2 ) INFORMATION FOR SEQ ID NO:2:

( i ) SEQUENCE CHARACTERISTICS:
( A ) LENGTH: 1012 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Thr Asn Leu Gln Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro
50 55 60

Gly Ser Ile Val Gly Ala His Tyr Thr Leu Gln Ser Asn Gly Asn Tyr
65 70 75 80

Lys Phe Asp Gln Met Leu Leu Thr Ala Gln Asn Leu Pro Ala Ser Tyr
85 90 95

Asn Tyr Cys Arg Leu Val Ser Arg Ser Leu Thr Val Arg Ser Ser Thr
100 105 110

Leu Pro Gly Gly Val Tyr Ala Leu Asn Gly Thr Ile Asn Ala Val Thr
115 120 125

Phe Gln Gly Ser Leu Ser Glu Leu Thr Asp Val Ser Tyr Asn Gly Leu
130 135 140

Met Ser Ala Thr Ala Asn Ile Asn Asp Lys Ile Gly Asn Val Leu Val
145 150 155 160

Gly Glu Gly Val Thr Val Leu Ser Leu Pro Thr Ser Tyr Asp Leu Gly
165 170 175

Tyr Val Arg Leu Gly Asp Pro Ile Pro Ala Ile Gly Leu Asp Pro Lys
180 185 190

Met Val Ala Thr Cys Asp Ser Ser Asp Arg Pro Arg Val Tyr Thr Ile
195 200 205

Thr Ala Ala Asp Asp Tyr Gln Phe Ser Ser Gln Tyr Gln Ser Gly Gly
210 215 220

Val Thr Ile Thr Leu Phe Ser Ala Asn Ile Asp Ala Ile Thr Ser Leu
225 230 235 240

-continued

| | | | | | | | | | | | | | | | |
|---|---|---|---|---|---|---|---|---|---|---|---|---|---|---|---|
| Ser | Val | Gly | Gly | Glu | Leu | Val | Phe | Lys | Thr | Ser | Val | Gln | Ser | Leu | Val |
| | | | | 245 | | | | | 250 | | | | | 255 | |
| Leu | Gly | Ala | Thr | Ile | Tyr | Leu | Ile | Gly | Phe | Asp | Gly | Thr | Ala | Val | Ile |
| | | | 260 | | | | | 265 | | | | | 270 | | |
| Thr | Arg | Ala | Val | Ala | Ala | Asn | Asn | Gly | Leu | Thr | Ala | Gly | Thr | Asp | Asn |
| | | 275 | | | | | 280 | | | | | 285 | | | |
| Leu | Met | Pro | Phe | Asn | Leu | Val | Ile | Pro | Thr | Asn | Glu | Ile | Thr | Gln | Pro |
| | 290 | | | | | 295 | | | | | 300 | | | | |
| Ile | Thr | Ser | Ile | Lys | Leu | Lys | Ile | Val | Thr | Ser | Lys | Ser | Gly | Gly | Leu |
| 305 | | | | | 310 | | | | | 315 | | | | | 320 |
| Glu | Gly | Asp | Gln | Met | Ser | Trp | Ser | Ala | Ser | Gly | Ser | Leu | Ala | Val | Thr |
| | | | | 325 | | | | | 330 | | | | | 335 | |
| Ile | His | Gly | Gly | Asn | Tyr | Pro | Gly | Ala | Leu | Arg | Pro | Val | Thr | Leu | Val |
| | | | 340 | | | | | 345 | | | | | 350 | | |
| Ala | Tyr | Glu | Arg | Val | Ala | Thr | Gly | Ser | Val | Val | Thr | Val | Ala | Gly | Val |
| | | 355 | | | | | 360 | | | | | 365 | | | |
| Ser | Asn | Phe | Glu | Leu | Ile | Pro | Asn | Pro | Glu | Leu | Ala | Lys | Asn | Leu | Val |
| | 370 | | | | | 375 | | | | | 380 | | | | |
| Thr | Glu | Tyr | Gly | Arg | Phe | Asp | Pro | Gly | Ala | Met | Asn | Tyr | Thr | Lys | Leu |
| 385 | | | | | 390 | | | | | 395 | | | | | 400 |
| Ile | Leu | Ser | Glu | Arg | Asp | Arg | Leu | Gly | Ile | Lys | Thr | Val | Trp | Pro | Thr |
| | | | | 405 | | | | | 410 | | | | | 415 | |
| Arg | Glu | Tyr | Thr | Asp | Phe | Arg | Glu | Tyr | Phe | Met | Glu | Val | Ala | Asp | Leu |
| | | | 420 | | | | | 425 | | | | | 430 | | |
| Asn | Ser | Pro | Leu | Lys | Ile | Ala | Gly | Ala | Phe | Gly | Phe | Lys | Asp | Ile | Ile |
| | | 435 | | | | | 440 | | | | | 445 | | | |
| Arg | Ala | Ile | Arg | Arg | Ile | Ala | Val | Pro | Val | Val | Ser | Thr | Leu | Phe | Pro |
| | 450 | | | | | 455 | | | | | 460 | | | | |
| Pro | Ala | Ala | Pro | Leu | Ala | His | Ala | Ile | Gly | Glu | Gly | Val | Asp | Tyr | Leu |
| 465 | | | | | 470 | | | | | 475 | | | | | 480 |
| Leu | Gly | Asp | Glu | Ala | Gln | Ala | Ala | Ser | Gly | Thr | Ala | Arg | Ala | Ala | Ser |
| | | | | 485 | | | | | 490 | | | | | 495 | |
| Gly | Lys | Ala | Arg | Ala | Ala | Ser | Gly | Arg | Ile | Arg | Gln | Leu | Thr | Leu | Ala |
| | | | 500 | | | | | 505 | | | | | 510 | | |
| Ala | Asp | Lys | Gly | Tyr | Glu | Val | Val | Ala | Asn | Leu | Phe | Gln | Val | Pro | Gln |
| | | 515 | | | | | 520 | | | | | 525 | | | |
| Asn | Pro | Val | Val | Asp | Gly | Ile | Leu | Ala | Ser | Pro | Gly | Ile | Leu | Arg | Gly |
| | 530 | | | | | 535 | | | | | 540 | | | | |
| Ala | His | Asn | Leu | Asp | Cys | Val | Leu | Arg | Glu | Gly | Ala | Thr | Leu | Phe | Pro |
| 545 | | | | | 550 | | | | | 555 | | | | | 560 |
| Val | Val | Ile | Thr | Thr | Val | Glu | Asp | Ala | Met | Thr | Pro | Lys | Ala | Leu | Asn |
| | | | | 565 | | | | | 570 | | | | | 575 | |
| Ser | Lys | Met | Phe | Ala | Val | Ile | Glu | Gly | Ala | Arg | Glu | Asp | Leu | Gln | Pro |
| | | | 580 | | | | | 585 | | | | | 590 | | |
| Pro | Ser | Gln | Arg | Gly | Ser | Phe | Ile | Arg | Thr | Leu | Ser | Gly | His | Arg | Val |
| | | 595 | | | | | 600 | | | | | 605 | | | |
| Tyr | Gly | Tyr | Ala | Pro | Asp | Gly | Val | Leu | Pro | Leu | Glu | Thr | Gly | Arg | Asp |
| | 610 | | | | | 615 | | | | | 620 | | | | |
| Tyr | Thr | Val | Val | Pro | Ile | Asp | Asp | Val | Trp | Asp | Asp | Ser | Ile | Met | Leu |
| 625 | | | | | 630 | | | | | 635 | | | | | 640 |
| Ser | Lys | Asp | Pro | Ile | Pro | Pro | Ile | Val | Gly | Asn | Ser | Gly | Asn | Leu | Ala |
| | | | | 645 | | | | | 650 | | | | | 655 | |
| Ile | Ala | Tyr | Met | Asp | Val | Phe | Arg | Pro | Lys | Val | Pro | Ile | His | Val | Ala |
| | | | 660 | | | | | 665 | | | | | 670 | | |

-continued

| | | | | | | | | | | | | | | | |
|---|---|---|---|---|---|---|---|---|---|---|---|---|---|---|---|
| Met | Thr | Gly | Ala | Leu | Asn | Ala | Tyr | Gly | Glu | Ile | Glu | Lys | Ile | Ser | Phe |
| | | 675 | | | | | 680 | | | | | 685 | | | |
| Arg | Ser | Thr | Lys | Leu | Ala | Thr | Ala | His | Arg | Leu | Gly | Leu | Lys | Leu | Ala |
| | 690 | | | | | 695 | | | | | 700 | | | | |
| Gly | Pro | Gly | Ala | Phe | Asp | Val | Asn | Thr | Gly | Pro | Asn | Trp | Ala | Thr | Phe |
| 705 | | | | | 710 | | | | | 715 | | | | | 720 |
| Ile | Lys | Arg | Phe | Pro | His | Asn | Pro | Arg | Asp | Trp | Asp | Arg | Leu | Pro | Tyr |
| | | | | 725 | | | | | 730 | | | | | 735 | |
| Leu | Asn | Leu | Pro | Tyr | Leu | Pro | Pro | Asn | Ala | Gly | Arg | Gln | Tyr | His | Leu |
| | | | 740 | | | | | 745 | | | | | 750 | | |
| Ala | Met | Ala | Ala | Ser | Glu | Phe | Lys | Glu | Thr | Pro | Glu | Leu | Glu | Ser | Ala |
| | | 755 | | | | | 760 | | | | | 765 | | | |
| Val | Arg | Ala | Met | Glu | Ala | Ala | Ala | Asn | Val | Asp | Pro | Leu | Phe | Gln | Ser |
| | 770 | | | | | 775 | | | | | 780 | | | | |
| Ala | Leu | Ser | Val | Phe | Met | Trp | Leu | Glu | Glu | Asn | Gly | Ile | Val | Ala | Asp |
| 785 | | | | | 790 | | | | | 795 | | | | | 800 |
| Met | Ala | Asn | Phe | Ala | Leu | Ser | Asp | Pro | Asn | Ala | His | Arg | Met | Arg | Asn |
| | | | | 805 | | | | | 810 | | | | | 815 | |
| Phe | Leu | Ala | Asn | Ala | Pro | Gln | Ala | Gly | Ser | Lys | Ser | Gln | Arg | Ala | Lys |
| | | | 820 | | | | | 825 | | | | | 830 | | |
| Tyr | Gly | Thr | Ala | Gly | Tyr | Gly | Val | Glu | Ala | Arg | Gly | Pro | Thr | Pro | Glu |
| | | 835 | | | | | 840 | | | | | 845 | | | |
| Glu | Ala | Gln | Arg | Glu | Lys | Asp | Thr | Arg | Ile | Ser | Lys | Lys | Met | Glu | Thr |
| | 850 | | | | | 855 | | | | | 860 | | | | |
| Met | Gly | Ile | Tyr | Phe | Ala | Thr | Pro | Glu | Trp | Val | Ala | Leu | Asn | Gly | His |
| 865 | | | | | 870 | | | | | 875 | | | | | 880 |
| Arg | Gly | Pro | Ser | Pro | Gly | Gln | Leu | Lys | Tyr | Trp | Gln | Asn | Thr | Arg | Glu |
| | | | | 885 | | | | | 890 | | | | | 895 | |
| Ile | Pro | Asp | Pro | Asn | Glu | Asp | Tyr | Leu | Asp | Tyr | Val | His | Ala | Glu | Lys |
| | | | 900 | | | | | 905 | | | | | 910 | | |
| Ser | Arg | Leu | Ala | Ser | Glu | Glu | Gln | Ile | Leu | Lys | Ala | Ala | Thr | Ser | Ile |
| | | 915 | | | | | 920 | | | | | 925 | | | |
| Tyr | Gly | Ala | Pro | Gly | Gln | Ala | Glu | Pro | Pro | Gln | Ala | Phe | Ile | Asp | Glu |
| | 930 | | | | | 935 | | | | | 940 | | | | |
| Val | Ala | Lys | Val | Tyr | Glu | Ile | Asn | His | Gly | Arg | Gly | Pro | Asn | Gln | Glu |
| 945 | | | | | 950 | | | | | 955 | | | | | 960 |
| Gln | Met | Lys | Asp | Leu | Leu | Leu | Thr | Ala | Met | Glu | Met | Lys | His | Arg | Asn |
| | | | | 965 | | | | | 970 | | | | | 975 | |
| Pro | Arg | Arg | Ala | Pro | Pro | Lys | Pro | Lys | Pro | Lys | Pro | Asn | Ala | Pro | Thr |
| | | | 980 | | | | | 985 | | | | | 990 | | |
| Gln | Arg | Pro | Pro | Gly | Arg | Leu | Gly | Arg | Trp | Ile | Arg | Thr | Val | Ser | Asp |
| | | 995 | | | | | 1000 | | | | | 1005 | | | |
| Glu | Asp | Leu | Glu | | | | | | | | | | | | |
| | 1010 | | | | | | | | | | | | | | |

INFECTIOUS BURSAL DISEASE VIRUS

RELATED APPLICATIONS:

This application is a continuation-in-part of U.S. application Ser. No. 07/727,370, filed Jul. 9, 1991, abandoned, which is a continuation of U.S. application Ser. No. 07/423,757, filed Oct. 18, 1989, abandoned, the entire disclosure of which is incorporated by reference herein, which is a continuation-in-part of U.S. application Ser. No. 07/227,311, filed Aug. 2, 1988, now U.S. Pat. No. 5,064,646, the entire disclosure of which is incorporated by reference herein.

BACKGROUND OF THE INVENTION

1. Field of the Invention

This invention relates to the poultry industry, and in particular, infectious bursal disease, a known scourge of this industry. Specifically, a novel virus is identified, and methods of using this virus and information associated therewith are disclosed. A neutralizing monoclonal antibody (Mab) specific for the virus, and a vaccine based thereon, are also disclosed.

2. Background of the Invention

Infectious bursal disease (IBD) has previously been identified as a significant economic drain in the poultry industry. This disease, which strikes chiefly at the chicken industry, is caused by virulent field viruses which cause a highly contagious, immunosuppressive disease condition. This condition, of course, exacerbates other infections in the chicken population. The disease is noted for its impact on young chickens, and is characterized by lesions in the lymphoidal follicles of the bursa of Fabricius.

In U.S. patent application Ser. No. 07/227,311, filed Aug. 2, 1988, the inventor herein reported the identification of a novel IBD virus not neutralized by any available vaccine and not neutralized by antibodies previously developed as sensitive to, and capable of neutralizing, all known viruses identified as inducing IBD. The entire disclosure of that application is incorporated herein by reference. Indeed, that application reports the deposition, under Budapest Treaty Conditions, of two viruses, at the Institute Pasteur, under accession numbers i-792 and i-793. This virus, now referred to as GLS, was detected by the use of monoclonal antibodies, particularly those identified as R63 and B69, expressed by hybridoma cell lines deposited under ATCC HB-9437 and HB-9490. These Mab's, identified as neutralizing monoclonal antibodies, comprise a passive vaccine against known strains of viruses inducing IBD and act as a means for detecting the presence of GLS virus, since the positive binding by a non-neutralizing antibody, such as B29, coupled with a negative reaction for R63 and B69 is proof of the GLS IBDV presence.

Thus, recent history in the poultry industry, particularly that along the eastern coast of the United States, reflects an increasingly large number of reports of outbreaks of infectious bursal disease, which are not fully prevented by any of the known vaccines, including those prepared from the monoclonal antibodies discussed above. Due to the severe economic strain placed on the poultry industry by these uncontrolled outbreaks, a significant degree of investigation of the cause of the outbreaks, and the reason for the failure of known vaccines to prevent such outbreaks, has been undertaken. No fault has been detected in the preparation of the vaccines, or their administration. Nonetheless, unchecked outbreaks continue to occur.

This continual outbreak is addressed, in part, by a vaccine developed using the virus addressed in U.S. application Ser. No. 07/227,311. This vaccine (GLS vaccine), now being successfully commercially introduced, alone or together with more conventional vaccines, provides protection against the dominant forms of IBDV infections.

New research, using monoclonal antibodies specific to 3 general categories of IBDV, has provided greater understanding of the IBDV. These developments are reported in the application identified above, U.S. application Ser. No. 07/432,752.

That application reports the development of neutralizing Mabs such as 179 and 8, available at the ATCC under deposit numbers HB-10158, HB-10174, and neutralizing against all previously known IBDV, and 57, ATCC deposit number HB-10156, neutralizing and specific to the GLS strain and variants. Recently research has identified yet a new IBDV in the field, not controlled by the GLS-vaccine. Monoclonal antibody 179 does not even react in vitro.

Thus, there is yet a new IBDV in the field, against which there is no current active vaccine, and against which no passive vaccine has yet been provided. This new virus, apparently a GLS variant and mutation thereof, given the Mab 57 in vitro binding, is currently uncontrolled. Protection for the poultry industry against this new IBDV is therefore a pressing need.

SUMMARY OF THE INVENTION

It has now been discovered that a new virus responsible for infectious bursal disease in poultry in the USA is a newly identified, GLS variant strain with altered recognition sites, such that none of the previously developed group reactive and neutralizing monoclonal antibodies are capable of neutralizing or binding to the virus. However, these monoclonal antibodies do neutralize and react with all known IBD vaccines of the current art. The virus has been isolated in essentially pure form and can be identified by the failure of monoclonal antibody 179 to bind thereto, while another common non-neutralizing antibody as well as standard polyclonal antisera available from the USDA will bind thereto in positive fashion and Mab 57 will bind it in vitro. Thus, the new virus may be recognized by a negative test. If Mab 179 will not bind, but B29, polyclonal antisera, or Mab 57 do react, the new GLS-variant virus, designated DS326, is present. Since 57 reacts with both GLS and DS 326, positive reaction of this Mab, alone, will not disseminate between the two viruses.

The new virus may be used in killed form as killed vaccines inducing antibodies resistant to the new virus, and may be used in attenuated form or otherwise genetically altered to prepare a live or killed vaccine.

Additionally, a new Mab, designated Mab 50 neutralizes the virus. The can be used to assay for the presence of the virus, and form an alternative vaccine for the passive immunization of young chickens.

BRIEF DESCRIPTION OF THE DRAWINGS

FIGS. 1–1E set forth the nucleotide sequence of the gene for expression of Mab 50 (SEQ ID NO: 1), as well as the amino acid sequence (SEQ ID NO: 2) therefor.

DETAILED DESCRIPTION OF THE INVENTION

As noted above, the new virus is not bound by any available monoclonal antibodies specific thereto. Thus, identification of the presence of the new virus cannot be achieved through conventionally available normal measures. However, by a combination of negative and positive testing, the presence of the virus and isolation of the virus can be achieved.

In particular, the monoclonal antibody designated 179 which neutralizes all previously identified serotype one IBD virus strains and at least one serotype two strain, gives negative results in an antigen capture-ELISA when reacted with the homogenized bursas drawn from chickens which yielded the new viruses. The same results were observed with Mabs B69 and R63, selective for the D78 virus strain and certain classic and Delaware viruses of an earlier art, once thought to be the prevalent strain in the United States. At the same time, another Mab designated B29, expressed by a hybridoma cell line deposited at the ATCC under accession number MB 9746, pursuant to Budapest Treaty conditions, which does not neutralize the virus, nevertheless binds to it, as well as to all known existing virus vaccines. Additionally, the polyclonal IBDV antisera used as a standard, and available from the USDA's national veterinary services laboratory in Ames, Iowa under designation ADU8701, binds, in the antigen capture ELISA, to the novel virus. Mab 57 will bind to the new virus, in vitro, as well as the GLS virus. Those of skill will identify non-neutralizing antibodies which bind to the virus, and can be directly produced as conventional monoclonal antibodies. The invention is not limited to any given Positive test factor. Since the overall size of the virus, in comparison to any available neutralization site is quite large, there will be a large potential field of such positive test factors and polyclonal antisera.

Thus, the presence of the virus can currently be best determined by negative testing in an antigen capture-ELISA for 179, and positive testing of either Mab 8, B29, 57, the polyclonal antisera or other positive Mab. It should be noted, however, that morphological or symptomatic verification of the presence of an IBD virus, coupled with a failure of the 179 to bind to an antigen sample, is clear evidence of the presence of the virus. Further, a positive reaction with Mab 57 indicates either GLS or DS 326 presence.

IDENTIFICATION OF THE VIRUS PRESENCE

To originally identify the presence of the new virus, chicken populations from a disaster farm were sampled. Bursas from the chicken populations were homogenized by placing one bursa in one ml of SGPA-EDTA buffer and grinding the mixture with a mortar and pestle until fluid-like consistency was obtained. This material was clarified by low speed centrifugation, and the supernatents were analyzed by an AC-ELISA.

In this assay, 96-well IMMULON 1 (polystyrene) plates (obtained from Dynatech, of Virginia) were coated with 0.1 ml of two ug/ml of protein A from *Staphlycoccus aureus* in a coating buffer. After 18 hours at 4° C., the plates were dumped. 1/10 dilutions of acid supernatents collected from hybridoma cultures secreting the 179, and 57 IBD virus specific Mabs were added in the phosphate buffered saline which contained TWEEN 20 (polyoxyethylene -20 sorbitan monolaurate)and 2% non-fat dried powdered milk, in alternating fashion. After a 24 hours reaction at 4° C., the plates were tapped dry and blocked for 30 minutes at room temperature. After blocking, the plates were emptied and tapped dry. 0.1 ml of serial dilutions of each sample of the homogenized bursal suspensions were added to the coated plates, and after incubation, the plates were emptied, tapped dry and washed three times for three minutes with PBS-T. Then, each well received 0.1 ml of a biotin labelled 179 Mab conjugate, which was diluted in PBS-T+NFDM. After an hour of incubation, the plates were again emptied and washed. Subsequently, 0.1 ml of a streptavidin-horseradish peroxidase conjugated was added to each well. After one hour of incubation the plates were again emptied and washed. This was followed by the addition of a TMB substrate. After a brief incubation period, the tests were read at 650 nm with the aid of an automated spectrophotometer. Thus, the biotinylated Mab was used to signal for positive reactions between the virus and 179, and 57 wells, while a similar AC-ELISA was performed with a polyclonal anti-IBDV sera was used to signal the B29 catches. Alternatively, biotinylated B29 could be used to the same effect. Further, any form of labeling of Mab or polyclonal antibodies may be used.

All strains showed negative for reactivity with 179, but were highly positive for the B29 Mab, which combines in a non-neutralizing fashion as well as reacting with neutralizing antibody 57.

As 179 is a neutralizing antibody for all previously identified IBD viruses, an assay employing only this as the positive non-neutralizing assay is adequate. The added use of B69 and R63 or 57 gives a higher confidence level, and can be used to further define and separate IBDV strains of the prior art.

As set forth above, the inventors have developed a new Mab, Mab 50, which is specific for, and neutralizes, virus DS326. As Mab 50 does not bind to, or neutralize, any other previously published, filed or USDA licensed vaccine strain of IBDV, or any other known IBDV virus, the specificity of Mab 50 allows one to assay for the presence of virus strain DS326, or confirm identification of the presence of virus strain DS326 according to the indirect method discussed above.

The murine Mab was developed according to the method set forth in U.S. Pat. No. 4,956,452. Specifically, hybridoma cell lines were prepared according to standard procedure, beginning with BALB/c mice, immunized with the DS326 virus strain, after purification. Hybridomas were prepared therefrom, and the resulting cell lines were assayed, through an enzyme-linked immunosorbant assay (ELISA) to identify those lines that binds to and neutralizes, the DS326 virus strain. The resulting cell line was cloned again and injected into pristane primed mice, to produce acidic fluid with higher titre values. Specific details as the propagation of the IBDV strain, production of the hybridoma, the ELISA, and the virus neutralization tests are set forth in U.S. Pat. No. 4,956,452, beginning at column 3, line 64 and continuing on to Column 5, line 68. The disclosure of this patent is incorporated herein by reference. The Mab 50 has been deposited under accession number ATCC HB 11123, on Sep. 16, 1992 by David Snyder. Further, the cell line is continuously available from Aurum Gudelsky Center, College of Veterinary Medicine, University of Maryland.

CONFIRMATION OF THE PURITY AND VIRULENCE OF THE VIRUS

Samples from the identified strain, which virus is expressed by the deposit made on Oct. 17, 1989, at the Collection Nationale de Culture de Micro-organismes (CNCM), Institut Pasteur, 28, rue du Dr. Roux, 75724 Paris Cedex 15, France, pursuant to Budapest Treaty conditions under accession number i-910 were pooled, and reacted with the 179 Mab and inoculated into SPF chickens. Five days after inoculation, these chickens, and non-inoculated chickens were necropsied. Those birds inoculated with the collected virus, referred to as DS 326 showed lesions consistent only with infectious bursal disease.

For certainty, antisera from the birds was taken at 11 days post-inoculation, and was tested by indirect ELISA and showed serologic conversion to IBDV, but to no other related poultry passed a second time in the presence of 179 with identical results. In both passages, on a scale of 0–9, reactivity with the B29 and 57 Mab was at level 9, and reactivity with 179 was at level 0. Thus, a pure preparation of a previously unidentified virus, not related to any known vaccine at the R63 and B69 neutralization sites, prepared from virus or otherwise, was identified. Preparation of additional monoclonal antibodies, protein information, and RNA analysis, has given rise to Mab 50 and is under further study. This information will provide the necessary base for the preparation of vaccines based on neutralizing, but non-toxic, recombinant virus-like proteins.

Until such "designed" vaccines becomes available, any of the isolated virus preparations each given the designation DS 326 can be used, in killed form, for the preparation of conventional killed vaccines, which do confer immunity against the new virus. The DS 326 strains may be prepared into a vaccine through common methods, which are not per se a part of this invention among the most prominent of which are heat killing and chemical killing, which preserves the essential form of the vaccine to enable the preparation, by the inoculated bird, of protective VN antibodies while rendering it non-virulent. Alternatively, there are known methods of attenuating viruses, including serial passage, cloning of the virus deleting sequences of nucleic acids and site-directed mutagenesis, which will allow the preparation of a live non-virulent virus vaccine. The vaccines may be prepared by simple incorporation of the selected virus derivative and suspending or incorporation of the selected virus derivative and suspending or mixing it in a carrier. Appropriate dosage values can be determined through routine trial and error techniques, sampling for antibody.

An alternative, passive immunization, particularly designed to achieve immunization in a uniform, standardized level, and to augment any maternally derived levels against DS326 IBDV field infection can be obtained by vaccinating 1-day old chicks with the vaccine comprising a pharmacologically acceptable carrier such as a phosphate buffered saline, cell culture medium, Mareti's virus vaccine diluent, etc., in which is present an amount of Mab 50 effective to provide enhanced protection for a period of time which allows the chicks to become more immunologically competent (about 2–3 weeks).

The necessary level of protection can be conferred by a single dose of the vaccine administered to a day-old chick having a Mab concentration of between 1 microgram and 1 milligram, or repeated vaccinations having a smaller effective dose, but carried out over time. If repeated vaccinations are used, the dosage level should range within 10 micrograms to 1 milligram. The concentration level needed to vaccinate older chickens is expected to increase with the weight of the bird.

FIGS. 1–1E contain a full recitation of the nucleotide sequence (SEQ ID NO: 1) for the gene responsible for the expression of the DS326 IBDV structural protein(s) recognized by Mab 50. Presented together with this information in FIG. 1 is the amino acid sequence (SEQ ID NO: 2) for the structural protein(s) recognized by the antibody. As noted above, one aspect of the utility of this Mab is its specificity for IBDV DS326, and it is apparent that modifications of the nucleotide sequence, or the resulting amino acid sequence, that delete critical recognition cites for the identifying characteristics of the DS326 virus will sufficiently alter Mab 50 as to render it incapable of neutralizing the virus, insufficient to support a vaccine, and potentially inadequate to identify the presence of the virus. Nonetheless, based on length of the amino acid sequence required for antibody binding, and studies applied to similar materials, it is expected that up to 10% of the amino acids of the structure can be modified or deleted, and up to 25% of the nucleotide sequence replaced or modified, particularly at the ends of the sequence, without loss of the binding and neutralizing ability of Mab 50. In particular, minor modifications which do not alter theconformal (quaternary) structure of the proteins) will not impede binding. Such modifications are clearly contemplated as one aspect of this invention.

As important as the preparation of the new vaccines is, there is now provided a method by which the presence of the virus can be identified in a given poultry population, by a relatively quick and efficient ELISA assay, which, if reaction to 179 is negative, while the reaction to a polyclonal vaccine, 57 or B29, is positive, then the presence of the virus is confirmed. B29 is expressed by a hybridoma cell line which has been deposited, under Budapest Treaty terms at the ATCC under accession number HB 9746. Alternatively, a positive ELISA using Mab 50 indicates the presence of DS326.

Obviously, numerous modification and variations of the present invention are possible in light of the above teachings. It is therefore to be understood that within the scope of the appended claims, the invention may be alternatively described or practiced otherwise than as specifically described herein.

What is claimed is:

1. A substantially pure preparation of the virus expressed by the cell line deposited at the Institute Pasteur under the accession number i-910.

2. A vaccine for the prevention of infectious bursal disease in poultry, comprising:
the virus of claim 1 and a pharmacologically acceptable carrier therefor.

3. The vaccine of claim 2, wherein said virus is in a killed form.

* * * * *